United States Patent [19]

Wittman et al.

[11] Patent Number: 5,395,849

[45] Date of Patent: Mar. 7, 1995

[54] HYBRID ANTITUMOR COMPOUNDS CONTAINING A CYCLIC ENEDIYNE AND A DNA-BINDER

[75] Inventors: Mark D. Wittman, Cheshire; David Langley, Meriden; John F. Kadow, Wallingford, all of Conn.

[73] Assignee: Bristol-Myers Squibb Company, New York, N.Y.

[21] Appl. No.: 132,026

[22] Filed: Oct. 5, 1993

[51] Int. Cl.$^6$ ............... A61k 31/40; A61k 31/44; C07D 209/10; C07D 207/50; C07D 401/08; C07D 233/58

[52] U.S. Cl. .................. 514/419; 514/422; 514/383; 514/397; 514/407; 514/343; 514/340; 514/341; 514/290; 514/314; 548/265.4; 548/311.1; 548/312.4; 548/313.7; 548/314.7; 548/364.1; 548/365.1; 548/492; 548/524; 546/276; 546/278; 546/279; 546/281; 546/101; 546/169; 546/175

[58] Field of Search ............... 548/524, 492, 265.4, 548/311.1, 312.4, 313.7, 314.7, 364.1, 365.1; 514/419, 422, 383, 407, 397, 290, 314, 343, 340, 341; 546/281, 276, 279, 278, 101, 169, 175

[56] References Cited

PUBLICATIONS

D. L. Boger and J. Zhou, "CDPI$_3$-Enediyne and CDPI$_3$-EDTA Conjugates: A New Class of DNA Cleaving Agents", *Journal of Organic Chemistry*, 58, pp. 3018-3024, 1993.

K. C. Nicolaou, et al, "Chemistry and Biology of Natural and Designed Enediynes", Proceedings of the National Academy of Sciences, USA, 90, pp. 5881-5888, 1993.

K. C. Nicolaou and W. M. Dai, "Chemistry and Biology of the Enediyne Anticancer Antibiotics", Angewandte Chemie, 30, No. 11, pp. 1387-1416, 1991.

Masahiko Tokuda, et al, "Synthesis of a Hybrid Molecule Containing Neocarzinostatin Chromophore Analogue and Minor Groove Binder", Tetrahedron Letters, 34, No. 4, pp. 669-672, 1993.

K. Toshima, et al, "Design, Synthesis and DNA Cleaving Profiles of Hybrids Containing the Novel Enediyne and Naturally Occurring DNA Intercalators", Journal of the Chemical Society, Chemical Communications, USA, pp. 1525-1527, 1993.

*Primary Examiner*—Mary C. Lee
*Assistant Examiner*—Joseph K. McKane
*Attorney, Agent, or Firm*—Willaim T. Han

[57] ABSTRACT

The present invention provides novel antitumor agents which are hybrid molecules consisting of a cyclic enediyne unit attached to a DNA-binding unit via a linker unit, and having the general formula (I)

$$D\text{—}(OCH_2)_m\text{—}O\text{—}(CH_2)_n\text{—}Ar\text{—}Y\text{—}CONH\text{—}B \qquad (I)$$

wherein D is a cyclic enediyne; B is a residue capable of binding to the minor groove of DNA; n is 0 and m is 1, is or n is 1 and m is 0 or 1; Ar is an aromatic residue selected from the group consisting of phenyl, naphthyl, pyridyl, quinolinyl and indolyl; and Y is a direct bond, —CH$_2$— or —CH=CH—; or a pharmaceutically acceptable salt thereof.

13 Claims, No Drawings

"5,395,849"

1

HYBRID ANTITUMOR COMPOUNDS CONTAINING A CYCLIC ENEDIYNE AND A DNA-BINDER

BACKGROUND OF THE INVENTION

1. Technical field

The present invention relates to novel compounds having tumor inhibiting and cytotoxic properties. More particularly, compounds of the present invention are hybrid molecules having an enediyne unit and a DNA-binding unit.

2. Background art

Cyclic enediyne moiety is present in complex antitumor antibiotics such as the esperamicins, calicheamicins, dynemicins, neocarzinostatin and kedarcidin. The unique molecular arrangement of these enediyne antibiotics and their interesting mode of action have attracted much research attention in the design and synthesis of simpler molecules with an enediyne unit that retain the DNA-interactive property of the natural products. See Nicolaou and Dai, "Chemistry and Biology of the Enediyne Anticancer Antibiotics" *Angewandte Chemie*, 1991, 30(11):1387–1416. Nicolaou and Dai also disclose a hybrid compound consisting of an enediyne unit modelled on the dynemicin core and a distamycin-type DNA minor groove binder. Another hybrid compound consisting of neocarzinostatin chromophore and a netropsin-type minor groove binder is reported in Tokuda et al, "Synthesis of a Hybrid Molecule Containing Neocarzinostatin Chromophore Analogue and Minor Groove Binder" *Tet. Lett.*, 1993, 34(4):669–672.

The present invention provides hybrid molecules of an enediyne and a DNA-binding unit interposed with a linker unit to enhance DNA binding.

SUMMARY OF THE INVENTION

The present invention provides a compound having formula (I)

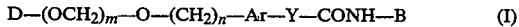

D—(OCH$_2$)$_m$—O—(CH$_2$)$_n$—Ar—Y—CONH—B         (I)

wherein D is a cyclic enediyne; B is a residue capable of binding to the minor groove of DNA; n is 0 and m is 1, or n is 1 and m is 0 or 1; Ar is an aromatic residue selected from the group consisting of phenyl, naphthyl, pyridyl, quinolinyl and indolyl; and Y is a direct bond, —CH$_2$— or —CH=CH—; or a pharmaceutically acceptable salt thereof.

The present invention also provides a method for inhibiting tumor in a mammalian host which comprises administering to said host a tumor inhibiting amount of a compound of formula (I).

Another aspect of the present invention provides a pharmaceutical composition which comprises a compound of formula (I) and a pharmaceutically acceptable carrier.

DETAILED DESCRIPTION OF THE INVENTION

In the application, "lower alkyl" refers to straight or branched carbon chains having from one to six carbon atoms. "Pharmaceutically acceptable salts" refers to acid addition salts, where a basic amino group is present on a compound of formula (I), with an inorganic acid such as hydrochloric acid, sulfuric acid, phosphoric acid and nitric acid, or with an organic acid such as acetic acid, propionic acid, maleic acid and an alkylsulfonic acid.

"Cyclic enediyne" refers to a carbocyclic residue having in its structural framework at least two carbon-carbon triple bonds and at least one carbon-carbon double bond.

Compounds of formula (I) are made up of three parts: an enediyne unit, D; a linker unit —(OCH$_2$)$_m$—O—(CH$_2$)$_n$—Ar—Y—CONH—; and a DNA binding unit, B. In compounds of formula (I) B is derived from a compound capable of binding to the minor groove of DNA (DNA binder) and said compound having a nitrogen atom capable of forming the amide bond of the linker unit. The DNA binder can be abbreviated as H$_2$N—B. The identity of the DNA binder is not particularly limited and may be for example a lexitropsin of formula (II)

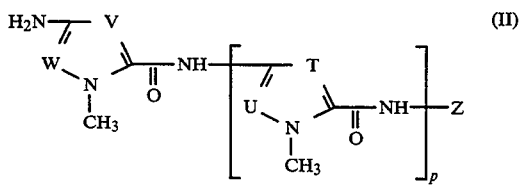

wherein T, U, V and W are independently CH or N; p is 1 or 2; and Z is a group selected from —CH(CH$_3$)CO$_2$R; —CH(CH$_3$)CONHCH(CH$_3$)CO$_2$R; —(CH$_2$)$_2$C(NH)NH$_2$; —(CH$_2$)$_2$C(O)NH$_2$; —(CH$_2$)$_q$NR$^1$R$^2$; and acridine—9—(1,4-phenylenediamine) compound of the formula

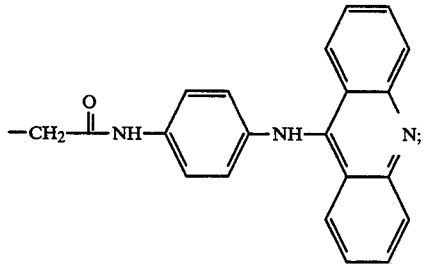

wherein R is hydrogen or lower alkyl; q is 2 or 3; R$^1$ and R$^2$ are independently H, lower alkyl, hydroxy lower alkyl, or amino lower alkyl.

These and other lexitropsins suitable for use in the present invention, as well as methods for their preparation, are disclosed in F. Debart et al, *J. Med. Chem.*, 1989, 32, pp. 1074–1083; C. Bailly et al, *J. Pharm. Sciences*, 1989, 78, p. 910; E. Nishiwaki, *Heterocycles*, 1990, 31, p. 1763; K. Krowicki et al, *J. Org. Chem.*, 1987, 52, p. 3493 (imidazole lexitropsins); K.E. Rao et al, *J. Org. Chem.*, 1990, 55, p. 728 (thiazole lexitropsins); and K.E. Rao et al, *Chem. Res. Toxicol.*, 1991, 4, p. 241 (1,3,5-triazole lexitropsins). G. M. Cohen et al, *J. Chem. Soc., Chem. Comm.*, 1992, p. 298 discloses linking spermidine to an antitumor agent, chlorambucil. All the above references are hereby incorporated by reference.

Other suitable DNA binders are for example 4-[p-[p-(4-quinolylamino)benzamido]-anilino]pyridine, also known as SN6999 (W. Leupin et al, *Biochemistry*, 1986, 25, pp. 5902–5910), the 6-amino derivative of SN6999 (J. Plowman et al, *Pharmacology*, 17, pp. 61–68), Hoechst 33258 amino analogs (M. P. Singh et al, *Chem. Res. Toxicol*, 1992, 5, pp. 597–607), oligonucleotide aminoalkylphosphonamides (B. L. Lee et al, *Biochemistry*, 1988, 27, p. 3197), N-(4-aminophenyl)indole-2-carboxamide, and pyrrolo[1,4]benzodiazepine derivatives (for example, see D. R. Langley et al, *J. Org. Chem.*, 1987, 52, p. 91).

In one preferred embodiment, the DNA-binding unit B is derived from a compound having the formula (II). In another preferred embodiment, B is derived from N-(4-aminophenyl)indole-2-carboxamide.

More preferably, B is derived from an oligo(N-methyl)pyrrole carboxamide derivative, for example, a netropsin or distamycin derivative having the formula (IIa)

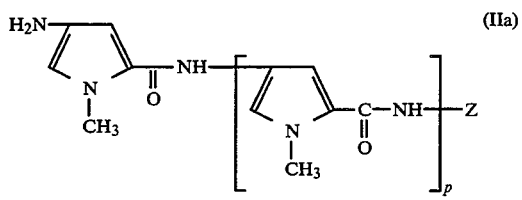

wherein p and Z are as previously defined. Even more preferred are oligo(N-methyl)pyrrole derivatives of formula (IIa) in which Z is —(CH$_2$)$_2$C(NH)NH$_2$ or —(CH$_2$)$_2$C(O)NH$_2$, or a pharmaceutically acceptable salt thereof.

The cyclic enediyne moiety D is also not particularly limited and is derived from a cyclic enediyne having a hydroxy group (D—OH) that allows the formation of ether or acetal linkage of the linker unit. Examples of cyclic enediyne are the 1,6-diyne-3-ene fragment (IIIa) found in neocarzinostatin chromophore, and the 1,5-diyne-3-ene fragment (IIIb) found in the chromophores of esperamicins/calicheamicins, dynemicin and kedarcidin.

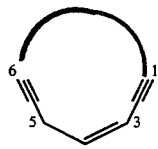

(IIIa)

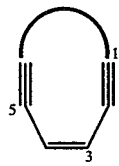

(IIIb)

Examples of known natural and synthetic enediynes and methods for their preparation can be found in the review by Nicolaou and Dai, "Chemistry and Biology of the Enediyne Anticancer Antibiotics," *Angewandte Chemie*, 1991, 30(11):1387–1416 and references cited therein.

In one preferred embodiment the D is derived from an enediyne having the formula (IV)

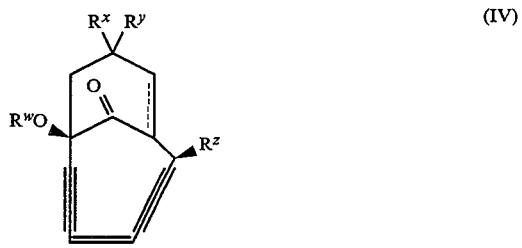

wherein ═══ is a double bond, a single bond, or an epoxy; one of $R^x$ or $R^y$ is hydrogen and the other is hydrogen or hydroxy; or $R^x$ and $R^y$ together is an oxo group; $R^w$ is hydrogen —C(O)R$^s$, —C(O)NR$^t$R$^u$ or —C(O)OR$^v$; $R^z$ is hydrogen, hydroxy, —OC(O)R$^s$, —OC(O)NR$^t$R$^u$ or —OC(O)OR$^v$; R$^s$ is hydrogen, C$_{1-8}$alkyl, C$_{3-6}$cycloalkyl, C$_{6-10}$aryl, C$_{7-14}$aralkyl or quinoxalyl; R$^t$ and R$^u$ are independently hydrogen, C$_{1-8}$alkyl, amino-substituted C$_{1-8}$alkyl, C$_{3-6}$cycloalkyl, C$_{6-10}$aryl, C$_{7-14}$aralkyl, pyridyl or quinoxalyl; R$^v$ is C$_{1-8}$alkyl, halo-substituted C$_{1-8}$alkyl, C$_{3-6}$cycloalkyl, C$_{6-10}$aryl or C$_{7-14}$aralkyl. Compounds of formula (IV) and methods for their preparation are disclosed in U.S. Pat. No. 5,198,560 which is hereby incorporated by reference.

In a more preferred embodiment D is derived from an enediyne having the formula (IVa) wherein R$^{z'}$ is hydrogen or OH.

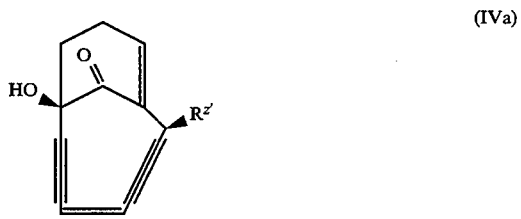

The linker unit is derived from an aromatic compound having at least two functionalities: (1) a carboxy group or an acylating equivalent thereof for the formation of the amide linkage to the DNA-binding unit; and (2) a functional group that can be utilized to form the ether or acetal linkage to the enediyne unit.

Ether/acetal forming functional groups are for example trichloroacetimidate (which forms ether linkage with D—OH), and methylthiomethyl ether (which forms acetal linkage with D—OH in the presence of N-iodosuccinimide and optionally a catalyst such as silver triflate). Or the functional group may be the hydroxy group, in which case D—OH is derivatized (e.g. to the corresponding methylthiomethyl ether).

Examples of precursors of the linker units are methyl 4-[(2,2,2-trichloro-1-imino)ethoxymethyl]phenylacetate (an imidate derived from 4-(hydroxymethyl)phenylacetic acid), and analogous imidates derived from methyl 3-(hydroxymethyl)-8-quinolinecarboxylate, methyl 6-(hydroxymethyl)-1-(or 2-)naphthalenecarboxylate, and methyl 6-(hydroxymethyl)-2-indolecarboxylate. Methyl 3-(hydroxymethyl)-8-quinolinecarboxylate may be prepared from methyl 3-bromo-8-quinolinecarboxylate (see Howitz and Schwenk, *Ber.*, 38:1280–1289, 1905) by treatment with n-butyllithium, dimethylformamide, followed by sodium borohydride. Methyl 6-(hydroxymethyl)-1-(or 2-)naphthalenecarboxylate may be similarly prepared from methyl 6-chloro-1-naphthalenecarboxylate (see Jacobs et al, *J. Org. Chem.*, 11:229–239, 1946) and methyl 6-bromo-2-naphthalenecarboxylate (see Anderson and Johnston, *J. Am. Chem. Soc.*, 65:239–242, 1943), respectively. Methyl 6-(hydroxymethyl)-2-indolecarboxylate is reported in Romero et al, *J. Med. Chem.*, 36:1505–1508, 1993.

The various hydroxy compounds mentioned above may be converted to the corresponding methylthiomethyl ether using dimethylsulfide/benzoyl peroxide, or dimethylsulfoxide/acetic anhydride. (See discussion infra for conversion of D—OH to D—OCH$_2$SCH$_3$.)

The preferred linker units are of formula (Va), (vb) or (Vc)

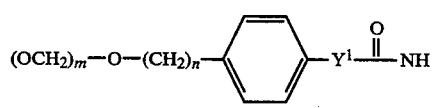
(Va)

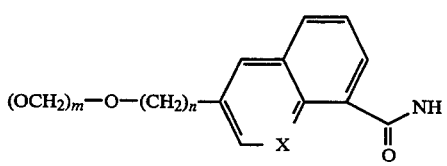
(Vb)

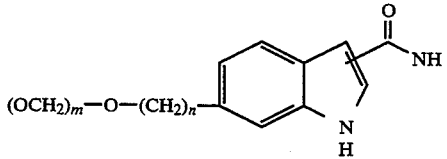
(Vc)

wherein X is CH or N; Y$^1$ is —CH$_2$— or —CH=CH—; and n and m are as defined above. More preferred linker units are of formula (Va) in which Y$^1$ is —CH$_2$—; n is 1 and m is 0 or 1.

More preferred embodiments of compounds of formula (I) are those wherein D is an enediyne of formula (IV); B is a group having the formula (II) and Ar—Y is a residue having the formula

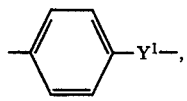
(Va')

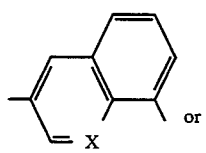
(Vb')

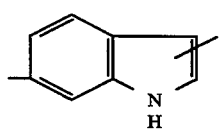
(Vc')

wherein X is CH or N, and Y$^1$ is —CH$_2$— or —CH=CH.

Even more preferred embodiments of compounds of formula (I) are those wherein D is an enediyne of formula (IVa); B is an oligo(N-methyl)pyrrolecarboxamide derivative, i.e., a compound of formula (IIa) wherein Z is —(CH$_2$)$_2$C(NH)NH$_2$ or —(CH$_2$)$_2$-C(O)NH$_2$; Ar—Y is a residue of formula (Va') wherein Y$^1$ is CH$_2$; n is 1; and m is 0 or 1.

Compounds of formula (I) may be prepared by reacting a DNA-binder, H$_2$N—B, with an enediyne-linker of the formula (VI), or an acylating equivalent thereof

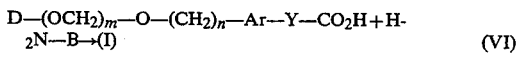

wherein B, D, Ar, Y, m and n are as previously defined. The amide bond formation between the enediyne-linker (VI) and the DNA-binder H$_2$N—B may be effected using methods generally known in the art. When a compound of formula (VI) is used in the carboxylic acid form, a coupling agent such as dicyclohexylcarbodiimide is added. Acylating equivalents of a compound of formula (VI) are for example the corresponding acid halide such as the acid chloride, a mixed anhydride, or an activated ester. An activated ester such as the pentafluorophenyl ester is preferably used. The reaction is carried out in an inert organic solvent such as dimethylformamide or an alcohol such as methanol at a temperature conducive to product formation. Typically, the reaction is carried out at ambient temperature and is complete within 24 hours. The product of formula (I) may be purified by conventional methods such as chromatography, crystallization and the like.

Compounds of formula (VI) are in turn derived from an enediyne D—OH and a functionalized HO—(CH$_2$-)$_n$—Ar—Y—CO$_2$P, or from a functionalized D—OH and HO—(CH$_2$)$_n$-Ar—Y—CO$_2$P, where n, Ar and Y are as previously defined and P is a carboxy protecting group. The functionality is one that is suitable to connect the linker unit and the enediyne unit via an ether or an acetal bond. For example, the hydroxy group can be converted to a trichloroacetimidate which is used to form the ether bond; or the hydroxy group can be converted to a methylthiomethyl ether which is used to form an acetal. The carboxy protecting group P may be one that is commonly used in organic synthesis; for example methyl, ethyl, allyl, haloethyl, benzyl, diphenylmethyl, triphenylmethyl esters. Other examples of carboxy protecting group may be found in Greene and Wuts, *Protective Groups in Organic Synthesis*, 2d Ed., John Wiley & Sons, 1991.

Again, preparative methods for ethers and acetals are well known in the art, and they can be used to make compounds of formula (VI). Thus, compounds of formula (VI) where m is 0 and n is 1 may be prepared by reacting D—OH with an imidate compound of the formula (VII)

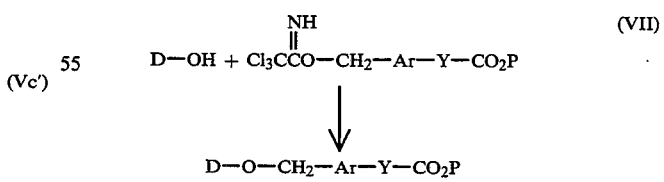
(VII)

The reaction is carried out in inert organic solvent such as ether, or halogenated hydrocarbon such as dichloromethane and in the presence of an acid such as trifluoromethanesulfonic acid. The reaction may be conducted at any temperature range suitable for product formation, typically at room temperature.

Compounds of formula (VII) may be prepared from compounds of formula (VIII)

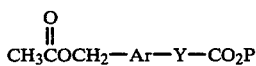

(VIII)

which are either known or may be readily prepared from known compounds by standard methods known to one skilled in the art of organic synthesis. Thus, a compound of formula (VIII) is treated with potassium carbonate in methanol, followed by cesium carbonate in trichloroacetonitrile to give the corresponding compound of formula (VII). It is contemplated that D—OH may also be similarly converted into the corresponding trichloroimidate which may then be reacted with HO—CH$_2$—Ar—Y—CO$_2$P to give the corresponding product of formula (VIII).

Compounds of formula (VI) wherein m is 1 may be prepared by treating a methylthiomethyl ether of an enediyne, D—OCH$_2$SCH$_3$, with N-iodosuccinimide (NIS) and a compound of the formula HO—(CH$_2$.)$_n$—Ar—Y—CO$_2$P where Ar, Y, P and n are as previously defined. The reaction is carried out in an inert organic solvent such as tetrahydrofuran or a halogenated hydrocarbon such as 1,2-dichloroethane or methylene chloride. The reaction may be conducted at a temperature ranging from about 0° C. to about 30° C., preferably at ambient temperature.

Methylthiomethyl ethers of enediynes (D—OCH$_2$SCH$_3$) are obtained by treating a solution of D—OH in dimethylsulfoxide with acetic anhydride at room temperature for about 10 to 24 hours. HO—(CH$_2$.)$_n$—Ar—Y—CO$_2$P are either known or can be easily derivatized from known compounds. It is also contemplated that HO—(CH$_2$)$_n$—Ar—Y—CO$_2$P may be similarly converted into the corresponding methylthiomethyl ether which may then be reacted with D—OH to provide compounds of formula (VI) wherein m is 1.

The enediyne and DNA-binding reactants may contain additional functional groups that may interfere with the desired reactions and therefore need to be blocked prior to carrying out such reactions. The blocking and deblocking of various types of functional groups are generally taught in standard textbooks such as Green and Wuts, *Protective Groups in Organic Synthesis*, 2d Ed., John Wiley & Sons, 1991. For example, the enediyne of formula (IVa) in which R$^3$ is OH may be attached to the linker unit via the tertiary hydroxy group if the secondary hydroxy group is first protected, e.g. by forming an ester.

Although the above-described process for the preparation of compounds of formula (I) involves first coupling the enediyne unit and the linker unit, and then coupling the resulting enediyne-linker with the DNA-binding unit, it is to be understood that this reaction sequence may be altered, i.e. first coupling the DNA-binding unit and the linker unit, then coupling the DNA-binder-linker with the enediyne unit.

Biological Evaluation

Sample compounds of the present invention were evaluated in in vitro cytotoxicity assay against HCT-116 human carcinoma cell line, and in in vivo P388 murine leukemia model.

Cytotoxicity was assessed in HCT116 human colon carcinoma cells by XTT (2 3-bis(2-methoxy-4-nitro-5-sulfpphenyl)-5-[(phenylamino)carbonyl]2H-tetrazolium hydroxide assay. Cells were plated at 4000 cells/well in 96 well microtiter plates and 24 hours later drugs were added and serial diluted. The cells were incubated at 37° C. for 72 hours at which time the tetrazolium dye, XTT, was added. A dehydrogenase enzyme in live cells reduces the XTT to a form that absorbs light at 450 nm which can be quantitated spectrophotometrically. The greater absorbance the greater the number of live cells. The results are expressed as an IC$_{50}$ which is the drug concentration required to inhibit cell proliferation (ie. absorbance at 450 nm) to 50% of that of untreated control cells.

Compounds of Examples 1, 2 and 4 were evaluated in this assay and they showed IC$_{50}$ values ranging from 0.452 to 6.19 mg/ml.

Compounds of Examples 1, 2 and 4 were also evaluated against transplantable P388 murine leukemia, generally following the protocols of the National Cancer Institute (see Cancer Chemotherapy Report, Part 3, 3, 1–103, 1972). CDF$_1$ female mice were implanted intraperitoneally with a tumor inoculum of 10$^6$ ascites cells of P388, and treated with various doses of test compounds. The compounds were administered intraperitoneally once on the day after tumor implantation. The ratio of median survival time for a treated group and that for the saline-treated control group was determined and expressed at %T/C. A compound with a %T/C value of greater or equal to 125 is considered to have significant antitumor activity. In this model the compounds tested showed maximum %T/C value of 130 at a dose level of 16 mg/kg/dose.

The invention includes within its scope pharmaceutical compositions containing an effective tumor-inhibiting amount of a compound of formula (I) in combination with an inert pharmaceutically acceptable carrier or diluent. Such compositions may also contain other active antitumor agents and may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

For use as an antitumor agent, compounds of formula (I) may be administered in a manner similar to that employed for other known antitumor agents such as mitomycin C, bleomycin or doxorubicin. Thus a compound of formula (I) may be administered for example, parenterally, enterally or locally. The optimal dosages and regimens of a compound of formula (I) for a given mammalian host can be readily ascertained by those skilled in the art. It will, of course, be appreciated that the actual dose of a compound of formula (I) used will vary according to the particular compound being used, the composition formulated, the mode of application and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease.

The present invention is illustrated by the following examples which are not to be construed as limiting the scope of the invention.

Preparation I

Methyl 4-[(2,2,2-trichloro-1-imino)ethoxymethyl]phenylacetate (7)

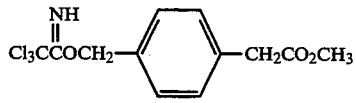

(a) To a solution of dicyclohexylcarbodiimide (8.9 g, 43.1 mol) and 4-(N,N-dimethylamino)pyridine (200 mg, 1.6 mmol) in 40 mL of acetonitrile was added 4-(acetoxymethyl)phenylacetic acid in 40 mL of acetonitrile (8.5 g, 40.7 mmol) followed by methanol (1.43 g, 44.6 mmol). After stirring for 30 min the solution was filtered and concentrated. The residue was chromatographed over silica gel (2:1 hexane/ethyl acetate) to give 2.0 g of a colorless oil.

The oil in 100 mL of methanol was stirred with a catalytic amount of $K_2CO_3$ for 1 hour, neutralized with Abmerlite (IR-120 (H+) resin, filtered and concentrated. The residue was chromatographed over silica gel (2:1 hexane/ethyl acetate) to give 1.3 g of methyl 4-(hydroxymethyl)phenylacetate as a colorless oil (18%).

$^1$H NMR (CDCl$_3$, 300 MHz)$\delta$7.32 (q, J=12 Hz, 4H), 4.69 (d, J=3 Hz, 2H), 3.71 (s, 3H), 3.65 (s, 2H).

(b) To a solution of the alcohol obtained in step (a) (1.31 g, 7.27 mmol) in 20 mL of dichloromethane was added $Cs_2CO_3$ (174 mg, 0.53 mmol) and trichloroacetonitrile (1.0 mL, 10 mmol). The solution was stirred for 8 hours, diluted with dichloromethane and washed with water and brine, dried over MgSO$_4$ and concentrated. The residue was chromatographed over silica gel (5:1 hexane/ethyl acetate) to give 1.39 g of the title product (59%).

$^1$H NMR (CDCl$_3$, 300 MHz) $\delta$8.40 (br s, 1H), 7.40 (d, J=7 Hz, 2H), 7.28 (d, J=7 Hz, 2H), 5.31 (s, 2H), 3.70 (s, 3H), 3.62 (s, 2H).

Preparation II

N-(4-aminophenyl)-1H-indole-2-carboxamide

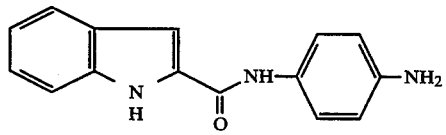

(a) A solution of N-(4-azidocarbonylphenyl)-1H-indole-2-carboxamide (492 mg, 1.56 mmol) in 50 mL of acetonitrile was refluxed for 2 hours and concentrated. The crude product was stirred with benzyl alcohol and pyridine. After 2 hours the solution was concentrated, absorbed onto silica gel using dimethylformamide, dried, and then placed on top of a silica gel column and eluted with hexane/ethyl acetate (2:1) and then 1:1 and then with straight ethyl acetate. The solution was concentrated and crystallized to give 316 mg of N-[(4-benzyloxycarbonyl)aminophenyl]-1H-indole-2-carboxamide (52%).

IR (KBr) 3402, 3322, 1706, 1652, 1540, 1518, 1404 cm$^{-1}$

This compound is in turn prepared according to the following reaction sequence:

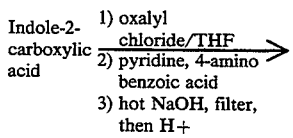

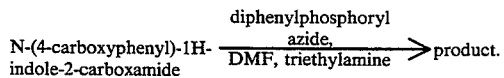

(b) A solution of the carbamate obtained in step (a) (240 m, 0,622 mmol) in 30 mL of ethanol was heated with cyclohexene (15 mL) and palladium hydroxide (120 mg) for 2 hours, filtered, and concentrated to give the title compound.

$^1$H NMR (300 MHz, d-6 DMSO)$\delta$11.61 (br s, 1H), 9.84 (br s, 1H), 7.62 (d, J=7.9 Hz, 1H), 7.42 (d, J=8.1, 1H), 7.37 (d, J=8.7 Hz, 2H), 7.29 (s, 1H), 7.17 (t, J=7.5 Hz, 1H), 7.02 (t, J=7.6 Hz, 1H), 6.54 (d, J=8.6 Hz, 2H), 4.94 (br s, 2H).

EXAMPLE 1

Bicyclodiynene-netropsin conjugate (1)

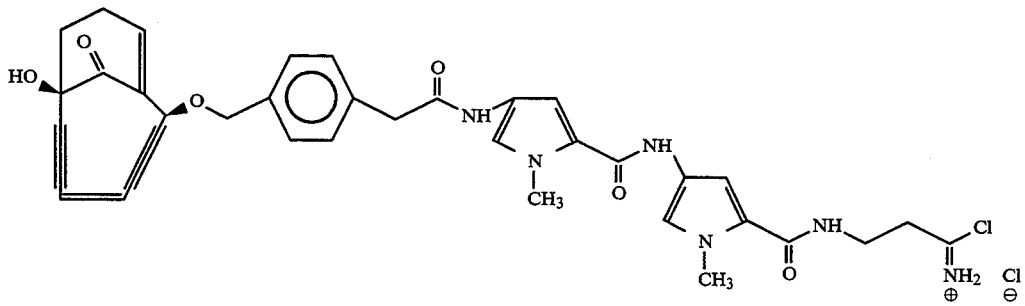

Method A (a) Preparation of 1-hydroxy-8-[4-[[(pentafluorophenoxy)carbonyl]methyl]]benzyloxy-bicyclo[7.3.1]-trideca-4,9-diene-2,6-diyn-13-one (9b)

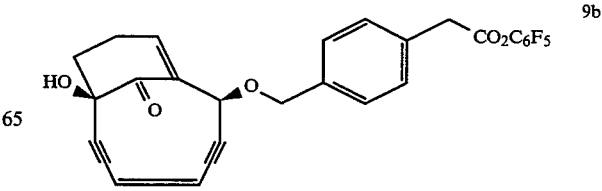

To a solution of 8-hydroxy-1-[(t-butyldimethylsilyl-)oxy]-bicylo[7.3.1]trideca-4,9-diene-2,6-diyn-13-one (6) (75 mg, 0.228 mmol) and methyl 4-[(2,2,2-trichloro-1-imino)ethoxymethyl]phenylacetate (7) (110 mg, 0.339 mmol) in 4 mL of anhydrous ether was added trifluoromethanesulfonic acid (10 μL+10 μL+10 μL, 0.339 mmol) in three portions. The solution was diluted with ethyl acetate and washed with saturated bicarbonate. The organic fraction was dried over MgSO$_4$, concentrated and the residue chromatographed over silica gel to give a mixture of 8-[4-[(methoxycarbonyl)methyl]benzyloxy]-1-[(t-butyldimethylsilyl)oxy]-bicyclo [7.3.1 ]trideca-4,9-diene-2,6-diyn-13-one (8a) and 1-hydroxy-8-[4-[(methoxycarbonyl)methyl]benzyloxy]-bicyclo[7.3.1]trideca-4,9-diene-2,6-diyn-13 -one (8b).

The silyl ether (8a) was dissolved in 4 mL of anhydrous ether and treated with 100 mL of trifluoromethanesulfonic acid, diluted with ethyl acetate and washed with saturated bicarbonate. The organic fraction was dried over MgSO$_4$ and the residue combined with compound 8b obtained above and chromatographed over silica gel (2:1 hexane/ethyl acetate) to give 50 mg (60%) of compound 8b as a colorless oil:

FABMS (NOBA) calcd for C$_{23}$H$_{21}$O$_5$ (M+H) 377.1389. Found: 377.1381.

IR (film) 3456, 2196 (w), 1734, 1708, 1258 cm$^{-1}$ $^1$H NMR (300 MHz, CDCl$_3$) δ7.30 (ABq, J=33.7, 8.1 Hz, 4H), 6.51 (t, J=2.7 Hz, 1H), 5.84 (m, 2H), 5.11 (s, 1H), 4.62 (s, 2H), 4.23 (s, 1H), 3.67 (s, 3H), 3.61 (s, 2H), 2.50 (m, 3H), 2.05 (m, 1H).

$^1$C NMR (75.5 MHz, CDCl$_3$) δ191.7, 172.0, 143.0, 135.9, 135.5, 133.7, 129.4, 128.5, 123.8, 123.5, 97.9, 96.3, 90.1, 89.4, 73.7, 72.1, 70.9, 52.1, 40.9, 32.0, 24.3.

To a solution of compound 8b (36 mg, 0.099 mmol) in 30 mL of ethanol and 20 mL of water was added barium hydroxide (74 mg, 0.22 mmol). The solution was stirred for 4 hrs, then acidified with 0.1N HCl and extracted with ethyl acetate. The organic fraction was dried over MgSO$_4$ and concentrated. The residue in 5 mL of ethyl acetate was stirred with pentafluorophenol (24 mg, 0,130 mmol) and dicyclohexylcarbodiimide (27 mg, 0,130 mmol) for 2 hrs, filtered and concentrated. The residue was chromatographed over silica gel (3:1 hexane/ethyl acetate) to give 20 mg (49%) of the title compound 9b, contaminated with excess phenol.

(b) Preparation of bicyclodiynene-netropsin conjugate (1)

To a solution of the crude pentafluorophenyl ester 9b (26 mg, 0,049 mmol) was added 4-amino-N-[5-[[(3-amino-3-iminopropyl)amino]carbonyl]-1-methyl-1H-pyrrol-3-yl]-1-methyl-1H-pyrrole-2-carboxamide monohydrochloride (10) (see J. W. Lown et al, *J. Org. Chem.*, 1985, 50:3774–3779; hereinafter des(-guanidinoacetyl)netropsin HCl) (20 mg, 0,054 mmol) and stirred 12 hrs. The solution was concentrated and purified over LH-20 (methanol). The eluant was concentrated and lyophilized to give 30 mg (85%) of the title compound 1 as a tan solid.

FABMS (NOBA) calcd for C$_{37}$H$_{38}$N$_7$O$_6$ (M+H) 676.2883. Found 676.2876:

IR (film) 3388 (br), 1692, 1646, 1582, 1532, 1518, 1436, 1260 cm$^{-1}$ $^1$H NMR (300 MHz, DMF) δ10.06(s, 1H), 9.86 (s, 1H), 8.90 (s, 2H), 8.47 (s, 2H), 8.20 (t, J=6.1 Hz, 1H), 7.30 (ABq, J=11.9, 8.2 Hz, 4H), 7.13 (d, J=7.8 Hz, 2H), 6.89 (dd, J=12.1, 1.6 Hz, 2H), 6.68 (br t, 1H), 6.07 (ABq, J=27.0, 9.6 Hz, 2H), 5.34 (s, 1H), 4.44 (m, 4H), 3.79 (s, 6H), 3.47 (q, J=6.5 Hz, 2H), 2.57 (br t, 6.5 Hz, 2H), 2.38 (m, 1H), 2.18 (m, 2H), 1.95 (m, 1H).

$^{13}$C NMR (75.5 MHz, DMSO) δ192.2, 169.0, 167.4, 161.5, 158.3, 142.6, 135.8, 128.8, 127.8, 124.3, 123.7, 2.7, 122.4, 122.1, 121.9, 118.2, 104.6, 104.1, 99.1, 98.0, 89.4, 88.6, 73.9, 72.2, 69.8, 42.4, 36.0, 36.0, 32.6, 32.3, 24.2.

Method B (a) preparation of 1-hydroxy-8-[4-[(pentafluorophenoxy)carbonyl]methyl]]benzyloxy-bicyclo[7.3.1]trideca-4,9-diene-2,6-diyn-13-one (9b)

To a solution of the alcohol 6 (208 mg., 0.63 mmol) and imidate 7 (300 mg, 0.92 mmol) in 5 mL of anhydrous ether was added trifluoromethanesulfonic acid (25 μL, 0.28 mmol). The solution was diluted with ethyl acetate and washed with saturated bicarbonate. The organic fraction was dried over MgSO$_4$, concentrated and the residue chromatographed over silica gel (5:1 hexane/ethyl acetate) to give compound 8a (184 mg, 59%) and 77 mg of recovered alcohol 1 (37%).

FABMS (NOBA) calcd for C$_{29}$H$_{34}$O$_5$SiNa (M+Na) 513. Found: 513.

IR (film) 2200 (w), 1738, 1720, 1256, 1162, 838, 782 cm$^{-1}$ $^1$H NMR (300 MHz, CDCl$_3$) δ7.29 (ABq, J=33.7, 8.0 Hz, 4H), 6.35 (t, J=3.5 Hz, 1H), 5.84 (ABq, J=15.9, 9.6 Hz, 2H), 5.07 (s, 1H), 4.64 (ABq, J=31.9, 12.2 Hz, 2H), 3.69 ( s, 3H) , 3.62 ( s, 2H) , 2.49 (m, 2H), 2.32 (m, 1H), 2.25 (m, 1H), 0.92 (s, 9H), 0.24 (s, 3H) , 0.19 ( s, 3H).

$^{13}$C NMR (75.5 MHz, CDCl$_3$) δ191.2, 172.0, 140.5, 136.5, 136.0, 133.6, 129.3, 128.6, 123.7, 123.0, 98.6, 96.9, 91.1, 88.8, 74.8, 73.9, 70.7, 52.1, 41.0, 34.7, 25.9, 24.7, 18.4, −2.8, −3.2.

To a solution of compound 8a (137 mg, 0,279 mmol) in 10 mL of ethanol with 5 mL of water added was added Ba(OH)$_2$ (175 mg, 0.55 mmol). The solution was stirred 2 h and acidified with iN HC$_1$ and extracted with ether. The etheral fraction was dried over MgSO$_4$ and concentrated. The residue was dissolved in 5 mL of acetonitrile and stirred with pentafluorophenol (61 mg, 0,331 mmol) and dicyclohexylcarbodiimide (80 mg, 0.39 mmol) for 2 h. The solution was filtered and concentrated and the residue chromatographed over silica gel (5:1 hexane/ethyl acetate) to give 1-[(t-butyldimethylsilyl)oxy]-8-[4-[[(pentafluorophenoxy)carbonyl]methyl]]benzyloxy-bicyclo[7.3.1]trideca-4,9-diene-2,6-diyn-13-one (9a) (112 mg, 62%).

DCIMS (isobutane) calcd for C$_{34}$H$_{32}$F$_5$O$_5$Si (M+H) 643. Found: 643.

IR (film) 1790, 1720, 1522, 1162, 1090, 1002 cm$^{-1}$ $^1$H NMR (300 MHz, CDCl$_3$) δ7.37 (ABq, J=30.0, 8.2 Hz, 4H), 6.34 (br t, J=3.2 Hz, 1H), 5.84 (ABq, J=15.5, 9.6 Hz, 2H), 5.07 (s, 1H), 4.64 (ABq, J=31.6, 12.2 Hz, 2H), 3.94 (s, 3H), 2.48 (m, 2H), 2.28 (m, 1H), 2.13 (m, 1H), 0.91 (s, 9H), 0.24 (s, 3H), 0.17 (s, 3H) .

$^{13}$C NMR (75.5 MHz, CDCl$_3$) δ191.2, 167.5, 140.6, 136.9, 136.5, 131.5, 129.3, 128.8, 123.7, 123.1, 98.4, 96.9, 91.1, 88.9, 74.8, 74.1, 70.6, 39.9, 34.7, 25.9, 24.7, 18.4, −2.9, −3.2.

To a solution of compound 9a in 16 mL of acetonitrile was added 4 mL of 48% HF. The solution was stirred for 16 h and diluted with chloroform and water. The chloroform fraction was separated and dried over MgSO$_4$ and concentrated. The residue was chromatographed over silica gel (3:1 hexane/ethyl acetate) to give compound 9b (67 mg, 72%)

FABMS (NBA) MH+ calcd for $C_{28}H_{18}F_5O_5$ 529.1074. Found: 529.1073.

IR (film) 3466 (br), 1788, 1706, 1522, 1118, 1088, 1002 cm$^{-1}$ $^1$H NMR (300 MHz, CDCl$_3$) δ7.40 (ABq, J=29.9, 8.1 Hz, 4H), 6.55 (br t, 1H), 5.86 (ABq, J=13.5, 9.7 Hz, 2H), 5.15 (s, 1H), 4.66 (s, 2H), 4.25 (s, 1H), 3.97 (s, 2H), 2.58–2.46 (m, 3H), 2.08 (m, 1H).

$^{13}$C NMR (75.5 MHz, CDCl$_3$) δ191.7, 167.4, 143.0, 136.7, 135.5, 131.7, 129.4, 128.7, 123.8, 123.6, 97.8, 96.3, 90.1, 89.5, 73.9, 72.1, 70.9, 39.9, 32.0, 24.3

(b) Preparation of compound 1

The pentafluorophenyl ester (46 mg, 0,087 mmol) was added des(guanidinoacetyl)netropsin HCl (10) (39 mg, 0,110 mmol) in 2 mL of dimethylformamide and stirred 16 hrs. The solution was purified over LH-20

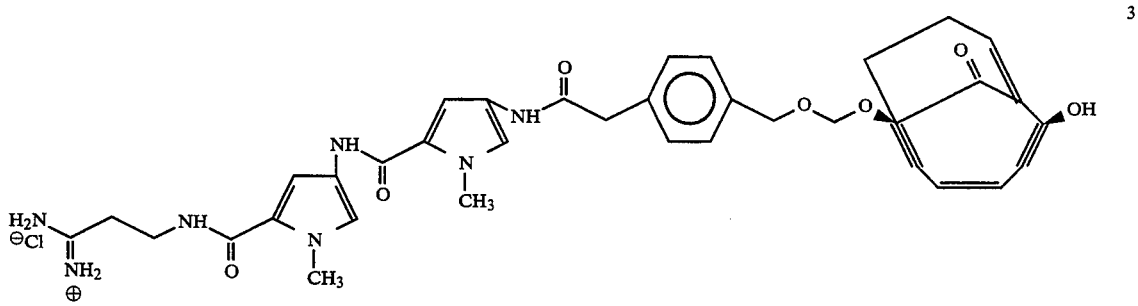

(methanol) to give 70 mg of 1 which was dissolved in water and lyophilized to give title compound 1 (53 mg, 87%) as a tan solid.

FABMS (NOBA) calcd for $C_{37}H_{38}N_7O_6$ (M+H) 676.2883.

EXAMPLE 2

Bicyclodiynene-netropsin conjugate (2)

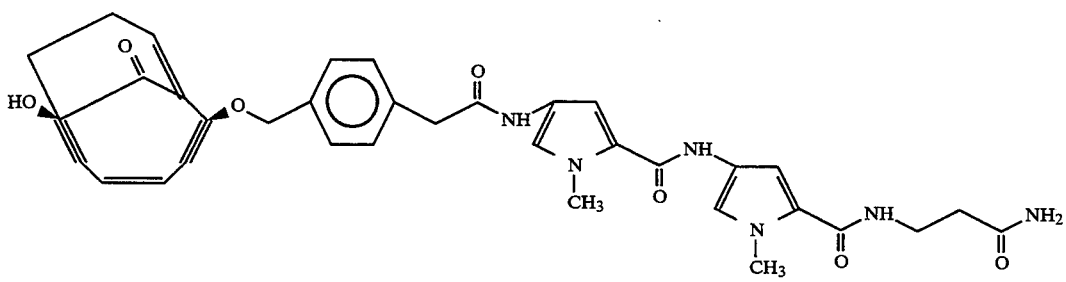

The pentafluorophenyl ester (9b) (54 mg, 0,102 mmol) and des(guanidinoacetyl)netropsin HCl (10) (68 mg, 0,186 mmol) were combined in dimethylformamide and stirred for 12 h. The solution was concentrated and chromatographed over silica gel (methanol/1% acetic acid) to give an oil which was frozen in methanol and water and lyophilized to give 40 mg (58%) of the title compound as an off-white solid.

FABMS (NOBA+NaI=KI) calcd for $C_{37}H_{36}N_6O_7$ (M+) 676.

IR (film) 3396 (br), 1634, 1592, 1540, 1436 cm$^{-1}$ $^1$H NMR (300 MHz, CDCl$_3$) δ10.06 (br s, 1H), 9.87 (br s, 1H), 8.26 (br t, J=5.4 Hz, 1H), 7.30 (ABq, J=11.5, 8.2 Hz, 4H), 7.16 (d, J=13.7 Hz, 2H), 5.34 (s, 2H), 4.44(ABq, J=16.7, 11.5 Hz, 2H), 3.79 (s, 6H), 3.44 (q, J=5.2 Hz, 2H), 2.39 (m, 1H), 2.21 (m, 2H), 1.97 (m, 1H).

$^{13}$C NMR (75.5 MHZ, DMSO) 192.2, 169.5, 167.4, 161.5, 158.4, 142.6, 135.8, 128.8, 127.8, 124.3, 123.8, 122.8, 122.4, 122.1, 121.9, 118.2, 104.5, 104.1, 99.2, 98.1, 89.4, 88.6, 73.9, 72.2, 69.9, 42.4, 36.1, 36.0, 32.7, 32.3, 24.2

EXAMPLE 3

Bicyclodiynene-netropsin conjugate (3)

(a) Preparation of 8-hydroxy-1-[4-[(pentafluorophenoxy)carbonyl]methyl]benzyloxymethoxy-bicyclo[7.3.1]-trideca-4,9-diene-2,6-diyn-13-one (14)

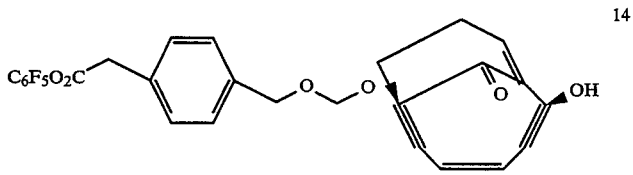

To a solution of compound 6 (175 mg, 0,533 mmol) in 10 mL tetrahydrofuran was added pyridine (0.20 mL, 2.47 mmol) and phenoxyacetyl chloride (0.17mL, 1.23 mmol) and stirred for 15 h. The solution was diluted with ether and washed with water and saturated bicarbonate. The organic fraction was dried over MgSO$_4$ and concentrated and the residue chromatographed over silica gel (10:1 hexane/ethyl acetate) to give 8-[(phenoxymethyl)carbonyloxy]-1-(t-butyldimethylsilyloxy)-bicyclo[7.3.1]trideca-4,9-diene-2,6-diyn-13-one (11a) (184 mg, 75%).

FABMS (NOBA) calcd for $C_{27}H_{30}SIO_5$ (M+Na) 485, (M+K) 501.

IR (film) 1766, 1716, 1252, 1220, 1174, 754 cm$^{-1}$ $^1$H NMR (300 MHz, CDCl$_3$) δ7.28 (m, 3H), 6.98 (m, 2H), 6.56 (t, J=3.0 Hz, 1H), 6.20 (s, 2H), 5.95 (d, J=9.6 Hz, 1H), 5.86 (dd, J=9.5, 1.5 Hz, 1H), 4.80 (ABq, J=28.6, 16.5 Hz, 2H), 2.52 (m, 2H), 2.30 (m, 1H), 2.13 (m, 1H), 0.93 (s, 9H), 0.24 (s, 3H), 0.19 (s, 3H).

$^{13}$C NMR (75.5 MHz, CDCl$_3$) δ190.9, 168.6, 157.7, 140.7, 135.0, 129.6, 124.3, 123.1, 121.7, 114.7, 97.1, 95.4, 91.06, 90.8, 74.6, 69.4, 64.9, 34.6, 25.9, 24.6, 18.4.

To a solution of compound 11a in 26 mL of acetonitrile was added 4 mL of 48% HF. The solution was stirred for 72 h. The solution was diluted with chloroform and washed with water. The organic fraction was dried over MgSO$_4$ and concentrated and the residue chromatographed over silica gel (5:1 hexane/ethyl acetate) to give 8-[(phenoxymethyl)carbonyloxy]-1-hydroxy-bicyclo[7.3.1]trideca-4,9-diene-2,6-diyn-13-one (11b) (116 mg).

FABMS (NOBA) calcd for C$_{27}$H$_{30}$SIO5 (M−H) 461. Found:

IR (film) 3474, 1764, 1706, 1176 cm$^{-1}$ $^1$H NMR (300 MHz, CDCl$_3$) δ7.29 (m, 2H), 6.95 (m, 3H), 6.70 (br t, 1H), 6.22 (s, 1H), 5.95 (d, J=9.6 Hz, 1H), 5.87 (dd, J=9.6, 1.5 Hz, 1H), 4.79 (ABq, J=16.5, 3.3 Hz, 2H), 4.05 (br s, 1H), 2.53 (m, 3H), 2.07 (m, 1H).

$^{13}$C NMR (75.5 MHz, CDCl$_3$) δ191.5, 168.5, 157.6, 143.2, 134.0, 129.6, 124.7, 123.2, 121.8, 114.7, 96.6, 94.8, 91.1, 90.1, 72.1, 68.9, 64.9, 31.9, 24.2.

To a solution of compound 11b (116 mg, 0.333 mmol) in 2 mL of dimethylsulfoxide was added 2 mL of acetic anhydride and the solution stirred for 16 h. The solution was diluted with ether and washed with water and saturated bicarbonate. The organic fraction was dried over MgSO$_4$ and concentrated. The residue was chromatographed over silica gel (5:1 hexane/ethyl acetate) to give 1-methylthiomethoxy-8-[(phenoxymethyl)carbonyloxy-bicyclo[7.3.1]trideca-4,9-diene-2,6-diyn-13-one (12) (121 mg) as tan oil (90%).

DCIMS (isobutane) M+H 409, M—SCH$_3$ 361, M—O$_2$CCH$_2$OPh 257

IR (film) 1764, 1712, 1176 cm$^{-1}$ $^1$H NMR (300 MHz, CDCl$_3$) δ7.28 (m, 2H), 6.98 (m, 3H), 6.57 (t, J=3.4 Hz, 1H), 6.20 (s, 1H), 6.00 (d, J=9.6 Hz, 1H), 5.90 (dd, J=9.6, 1.5 Hz, 1H), 5.03 (ABq, J=72.2, 10.9 Hz, 2H), 4.79 (ABq, J=23.7, 16.5 Hz, 2H), 2.59 (m, 2H), 2.43 (m, 1H), 2.28 (m, 3H) 2.20 (m, 1H).

$^{13}$C NMR (75.5 MHz, CDCl$_3$) δ190.8, 168.5, 157.7, 141.0, 135.1, 129.6, 124.2, 123.8, 121.7, 114.7, 95.6, 94.4, 92.7, 91.0, 78.4, 72.2, 69.2, 64.8, 32.2, 24.5, 14.7.

To a solution of compound 12 (100 mg, 0.24 mmol) in 10 mL of ethanol with 0.5 mL of ethyl acetate added was added barium hydroxide (1 mg, 1%) and the solution stirred for 2 h. The solution was neutralized with Dowex 50W-8X acidic resin, filtered and concentrated. The residue was chromatographed over silica gel (3:1 hexane/ethyl acetate) to give 8-hydroxy-1-methylthiomethoxy-bicyclo[7.3.1]trideca-4,9-diene-2,6-diyn-13-one (13) (56 mg, 85%).

DCIMS (isobutane) 275 (M+H), 257 (M—OH), 227 (M—SCH$_3$).

IR (film) 3474 (br), 1688, 1116 cm$^{-1}$ $^1$H NMR (300 MHz, CDCl$_3$) δ6.41 (t, J−4.1 Hz, 1H), 5.88 (s, 2H), 5.23 (d, J=10.8 Hz, 1H), 5.02 (ABq, J=44.3, 11.0 Hz, 2H), 4.67 (d, J=10.8 Hz, 1H), 2.58–2.52 (m, 2H), 2.46–2.39 (m, 1H), 2.24 (s, 3H), 2.21–2.13 (m, 1H).

$^{13}$C NMR (75.5 MHz, CDCl$_3$) δ195.6, 139.3, 136.6, 124.9, 122.4, 101.0, 95.9, 91.6, 87.3, 79.1, 72.4, 68.8, 31.8, 24.6, 14.7.

To a solution of compound 13 (142 mg, 0.518 mmol) in 10 mL of methylene chloride with 4Å sieves was added pentafluorophenyl 4-hydroxymethylphenyl acetate (574 mg, 1.73 mmol) and N-iodosuccinimide (126 mg, 0.56 mmol). The solution was cooled to 0° C. and triethylsilyl triflate was added (9 μL, 0.040 mmol). After 5 min at 0° C. the solution was quenched with excess triethylamine, diluted with ether and washed with 10% NaS$_2$O$_8$, saturated bicarbonate and brine. The organic fraction was dried with MgSO$_4$ concentrated and the residue chromatographed over silica gel (3:2 pentane/ether) to give the title compound 14 (156 mg, 54%).

FABMS (NOBA) 581 (M+Na), 597 (M+K).

IR (film) 3484 (br), 1788, 1690, 1520, 1090, 1056, 1000, 754 cm$^{-1}$ $^1$H NMR (300 MHz, CDCl$_3$) δ7.32 (ABq, J=10.6, 8.4 Hz, 4H), 6.43 (t, J=3.0 Hz, 1H), 5.85 (s, 2H), 5.23 (d, J=10.9 Hz, 1H), 5.20 (ABq, J=48.1, 7.2 Hz, 2H), 4.70 (ABq, J=19.5, 12.1 Hz, 2H), 4.70 (d, J=11.0 Hz, 1H), 3.94 (s, 2H), 2.58–2.44 (m, 3H), 2.27–2.17 (m, 1H).

$^{13}$C NMR (75.5 MHz, CDCl$_3$) δ194.5, 167.4, 139.4, 137.5, 136.7, 131.4, 129.3, 128.3, 124.8, 122.5, 100.9, 94.8, 92.6, 92.0, 87.3, 78.2, 69.7, 68.8, 39.9, 32.0, 24.5.

(b) Preparation of bicyclodiynene-netropsin conjugate (3)

To a solution of compound 13 (57 mg, 0.1 mmol) in 2 mL dimethylformamide was added des(-guanidinoacetyl)netropsin HCl (45 mg, 0.13 mmol) and the solution stirred 12 h. The reaction mixture was placed directly on an LH-20 column and eluted with methanol to give 73 mg of and oil (quant). The residue was then frozen in a mixture of methanol and water and lyophilized to give compound 3 (50 mg, 69%) as a tan solid.

FABMS (NOBA) 706 (M+H), 728 (M+Na), 744 (M+K).

IR (film) 3388 (br), 2188, 1690, 1640, 1518 cm$^{-1}$ $^1$H NMR (300 MHz, d7-DMF) δ10.32 (s, 1H), 10.05 (s, 1H), 9.43 (s, 2H), 9.41 (s, 2H), 8.51 (br t, 1H), 7.41-7.33 (m, 5H), 7.25 (d, J=1.6 Hz, 1H), 7.07 (dd, J=4.0,1.6 Hz, 2H), 6.72 (br t, 1H), 6.15 (ABq, J=18.9, 9.7 Hz, 2H), 5.49 (m, 1H), 5.22 (m, 1H), 5.17 (ABq, J=18.0,6.8 Hz, 2H), 4.69 (ABq, J=24.3, 12.0 Hz, 2H), 3.91 (s, 3H), 3.90 (s, 3H), 3.70 (q, J=6.2 Hz, 2H), 2.88 (t, J=6.2 Hz, 2H), 2.73–2.42 (m, 3H), 2.25 (m, 1H).

$^{13}$C NMR (75.5 MHz, CD$_3$OD) δ194.8, 171.0, 164.4, 161.4, 141.6, 138.6, 138.0, 136.5, 130.5, 130.1, 129.3, 128.3, 125.7, 124.6, 123.9, 123.7, 123.4, 123.3, 120.9, 120.7, 106.78, 106.0, 101.8, 95.6, 93.5, 93.3, 88.3, 79.7, 70.7, 69.3, 43.8, 37.5, 36.8, 34.5, 33.1, 25.5.

EXAMPLE 4

Bicyclodiynene-netropsin conjugate (4)

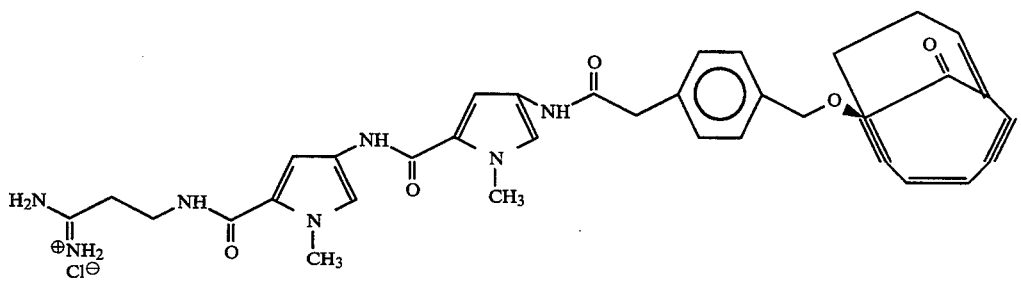

(a) preparation of 1-[4-(pentafluorophenoxy)carbonyl]-methyl]benzyloxy-bicyclo[7.3.1]trideca-4,9-diene-2,6-diyn-13-one (17)

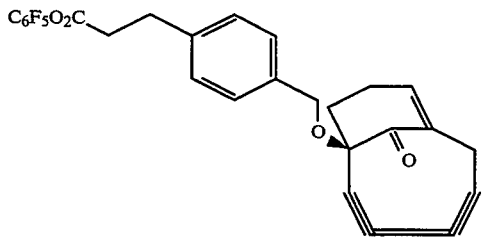

To a solution of 1-hydroxy-bicyclo[7.3.1]trideca-4,9-diene-2,6-diyne-13-one (15) (222 mg, 1.11 mmol) in 8 mL of anhydrous ether was added compound 7 (593 mg, 1.83 mmol) followed by trifluoromethanesulfonic acid (48 μL, 0.54 mmol). The solution was stirred for 30 min, diluted with ether, washed with water and dried over Na₂SO₄. The residue was chromatographed over silica gel (5:1 hexane/ether) and then rechromatographed over silica gel (12:1 benzene/ether) to give 1-[4-(methoxycarbonyl)methyl]benzyloxy-bicyclo[7.3.1]trideca-4,9-diene-2,6-diyn-13-one (16) (221 mg, 55%) as an oil which, as shown by proton NMR, was contaminated with a byproduct arising from the imidate. The benzyl ether 16 was not characterized but was carried on to the next step.

To a solution of compound 16 (96 mg, 0.265 mmol) in 10 mL of tetrahydrofuran along with 2 mL of water was added barium hydroxide (60 mg, 0.316 mmol). The solution was stirred for 1 h and acidified with 0.1N HCl and extracted with ethyl acetate. The ethyl acetate solution was dried over MgSO₄ and concentrated. The residue was dissolved in 5 mL of ethyl acetate and stirred with pentafluorophenol (56 mg, 0.30 mmol) and dicyclohexylcarbodiimide (68 mg, 0.33 mmol) for 2 h. The solution was filtered and concentrated and the residue chromatographed over silica gel (4:1 hexane/ethyl acetate) to give the title compound 17 (50 mg, 37%).

FABMS (NOBA) M+Na calcd. for $C_{28}H_{19}O_4F_5Na$ 537.1101. Found: 537.1089.

IR (film) 2200 (w), 1788, 1726, 1520, 1090, 1002 cm$^{-1}$ $^1$H NMR (300 MHz, CDCl₃) δ7.37 (ABq, J=37.3, 8.2 Hz, 4H), 5.90 (s, 2H), 4.91 (ABq, J=77.6, 11.4 Hz, 2H), 3.94 (s, 2H), 3.21 (dd, J=17.6, 3.4 Hz, 1H), 2.71 (m, 2H), 2.47 (m, 2H), 2.07 (m, 2H), 1.75 (m, 2H). $^{13}$C NMR (75.5 MHz, CDCl₃) δ204.9, 167.4, 138.5, 131.1, 129.1, 128.4, 125.1, 121.3, 100.5, 94.2, 94.0, 83.6, 78.0, 69.1, 49.2, 39.9, 34.3, 24.3, 23.9, 18.9.

To a solution of compound 17 (57 mg, 0.11 mmol) in 3 mL of dimethylformamide was added the des(-guanidinoacetyl)netrpsin HCl (10) (49 mg, 0.13 mmol) and the solution stirred for 18 h. The solution was concentrated and the residue dissolved in methanol and run through an LH-20 size exclusion column to give 100 mg of an oil (quant.) which was lyophilized from methanol/water to give the title compound 4 as a tan solid.

FABMS (NOBA) M+H calcd. for $C_{37}H_{40}N_7O_5$ 662.3091. Found: 662.3083.

IR (KBr) 3396 (br), 2200, 1718, 1690, 1646, 1582, 1532, 1518, 1466, 1436, 1404 cm$^{-1}$ $^1$H NMR (300 MHz, d7-DMF) δ10.14 (s, 1H), 9.89 (s, 1H), 9.00 (s, 2H), 8.68 (s, 2H), 8.22 (br t, 1H), 7.14 (d, J=12.5 Hz, 2H), 6.89 (dd, J=8.8, 1.7 Hz, 2H), 6.12 (s, 2H), 4.66 (ABq, J=59.4, 11.2 Hz, 2H), 3.78 (s, 6H), 3.54 (s, 2H), 3.47 (br q, J=6.0 Hz, 2H), 2.99 (dd, J=17.7, 3.5 Hz, 1H), 2.79 (m, 1H), 2.60 (m, 4H), 2.33 (m, 1H), 1.97 (m, 2H), 1.71 (m, 2H).

$^{13}$C NMR (75.5 MHz, d6-DMSO) δ204.4, 178.0, 169.1, 167.4, 161.5, 158.4, 136.7, 135.6, 128.7, 127.6, 125.6, 122.4, 122.1, 121.8, 118.2, 104.7, 104.1, 101.1, 94.3, 93.6, 83.6, 77.6, 67.9, 48.3, 42.3, 36.0, 35.9, 33.0, 32.6, 23.6, 23.3, 18.2.

EXAMPLE 5

Bicyclodiynene indole conjugate (1)

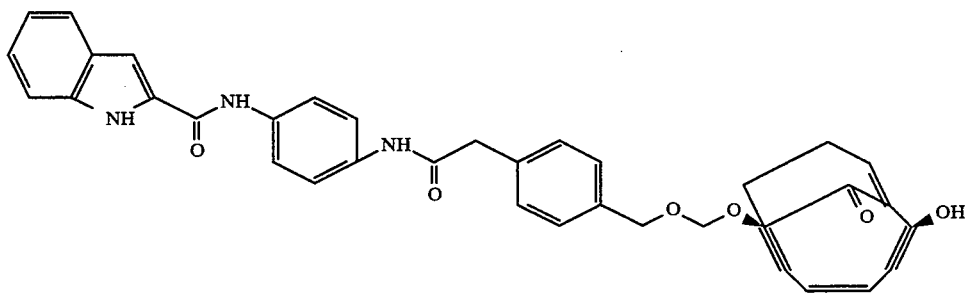

To a solution of compound 14 (88 mg, 0.157 mmol) in 2 mL dimethylformamide was added the N-(4-aminophenyl)-1H-indole-2-carboxamide (40 mg, 0.155 mmol). The solution was stirred for 48 h and diluted with ethyl acetate and washed with water, dried over MgSO$_4$ and concentrated. The residue was dissolved in a little acetone and a slurry made with silica gel. The slurry was evaporated to adsorb the reaction on the silica. The silica was then placed on a column of silica and eluted (1:1 hexane/ethyl acetate) to give the title compound 1 (15 mg, 15%).

FABMS (NOBA) MH+ calcd for C$_{38}$H$_{32}$N$_3$O$_6$ 626.2291. Found: 626.2278.

IR(KBr) 3600–3200 (br), 1664, 1644, 1548, 1514, 1404, 1384 cm$^{-1}$ $^1$H NMR (300 MHz, d7-DMF) δ11.75 (s, 1H), 10.30 (s, 1H), 10.26 (s, 1H), 7.85 (d, J=9.0 Hz, 1H), 7.84 (d, J=8.9 Hz, 1H), 7.71 (d, J=9.0 Hz, 2H), 7.69 (d, J=8.9 Hz, 1H), 7.58 (d, J=8.2 Hz, 1H), 7.50 (s, 1H), 7.39 (ABq, J=16.4, 8.2 Hz, 4H), 7.26 (t, J=8.1 Hz, 1H), 7.09 (t, J=7.9 Hz, 1H), 6.14 (ABq, J= 19.6, 9.6 Hz, 2H), 5.47 (s, 1H), 5.18 (ABq, J=19.1, 6.9 Hz, 2H), 4.70 (ABq, J=24.8, 11.9 Hz, 2H), 3.73 (s, 2H), 2.69–2.43 (m, 3H), 2.23 (m, 1H).

$^{13}$C NMR (75.5 MHz, d7-DMF) δ193.8, 169.6, 160.2, 140.9, 138.3, 137.9, 137.7, 137.3, 136.3, 135.6, 132.6, 129.8, 127.2, 125.5, 124.4, 123.6, 122.4, 120.9, 120.6, 120.0, 112.9, 104.0, 102.6, 94.8, 93.7, 92.8, 87.5, 79.0, 69.9, 68.5, 44.0, 32.5, 24.9.

We claim:

1. compound having the formula

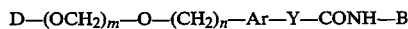

D—(OCH$_2$)$_m$—O—(CH$_2$)$_n$—Ar—Y—CONH—B wherein D is a radical of the formula

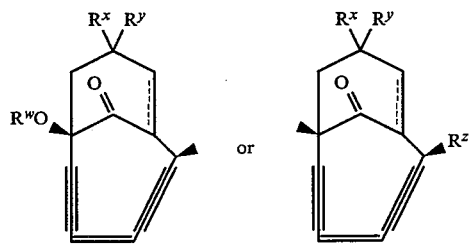

wherein ===== is a double bond, a single bond, or an epoxy; one of R$^x$ or R$^y$ is hydrogen and the other is hydrogen or hydroxy; or R$^x$ and R$^y$ together is an oxo group; R$^w$ is hydrogen, —C(O) R$^s$, —C(O)NR$^t$R$^u$ or —C(O)OR$^v$; R$^z$ is hydrogen, hydroxy, —OC(O)R$^s$, —OC(O)NR$^t$R$^u$ or —OC(O)OR$^v$; R$^s$ is hydrogen, C$_{1-8}$alkyl, C$_{3-6}$cycloalkyl, C$_{6-10}$aryl, C$_{7-14}$aralkyl or quinoxalyl; R$^t$ and R$^u$ are independently hydrogen, C$_{1-8}$alkyl, amino-substituted C$_{1-8}$alkyl, C$_{3-6}$cycloalkyl, C$_{6-10}$aryl, C$_{7-14}$aralkyl, pyridyl or quinoxalyl; R$^v$ is C$_{1-8}$alkyl, halo-substituted C$_{1-8}$alkyl, C$_{3-6}$cycloalkyl, C$_{6-10}$aryl or C$_{7-14}$aralkyl; B is a radical of the formula

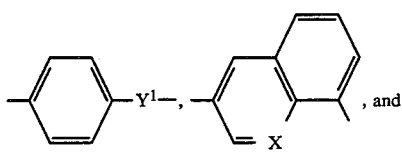

wherein T, U, V and W are independently CH or N; p is 1 or 2; and Z is a group selected from —CH(CH$_3$)CO$_2$R; —CH(CH$_3$)CONHCH(CH$_3$)CO$_2$R; —(CH$_2$)$_2$C(NH)NH$_2$; —(CH$_2$)$_2$C(O)NH$_2$; —(CH$_2$)$_q$NR$^1$R$^2$; and acridine-9-(1,4-phenylenediamine) radical of the formula wherein R is hydrogen or lower alkyl; q is 2 or 3; R$^1$ and R$^2$ are independently H, lower alkyl, hydroxy lower alkyl, or amino lower alkyl; n is 0 and m is 1, or n is 1 and m is 0 or 1; Ar is an aromatic residue selected from the group consisting of phenyl, naphthyl, pyridyl, quinolinyl and indolyl; and Y is a direct bond, —CH$_2$— or CH=CH; or a pharmaceutically acceptable salt thereof.

2. compound of claim 1 wherein Ar—Y is selected from

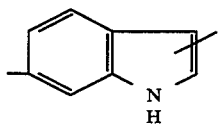

wherein X is CH or N, and $Y^1$ is —$CH_2$— or —CH=CH—.

3. A compound of claim 1 wherein $R^w$ is hydrogen; and $R^z$ is hydrogen or hydroxy.

4. A compound of claim 1 wherein B is a radical of the formula

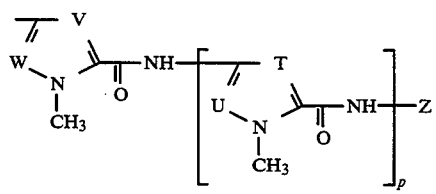

wherein p is 1 or 2 and Z is selected from a group consisting of —$CH(CH_3)CO_2R$; —$CH(CH_3)CONHCH(CH_3)CO_2R$; —$(CH_2)_2C(NH)NH_2$; —$(CH_2)_2C(O)NH_2$; —$(CH_2)_qNR^1R^2$; and acridine-9-(1,4-phenylenediamine) radical of the formula

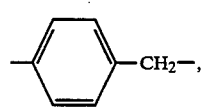

wherein R is hydrogen or lower alkyl; and q is 2 or 3; $R^1$ and $R^2$ are independently H, lower alkyl, hydroxy lower alkyl, or amino lower alkyl.

5. A compound of claim 1 wherein Ar—Y is

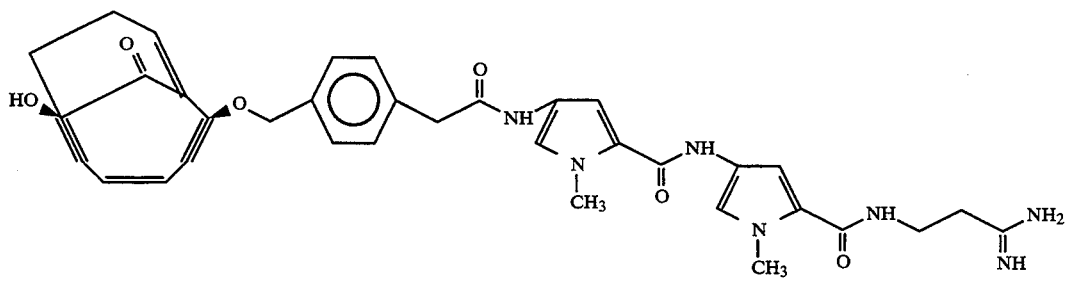

n is 1 and m is 0 or 1.

6. A compound of claim 1 wherein Z is —$(CH_2)_2C(NH)NH_2$ or —$(CH_2)_2C(O)NH_2$.

7. A compound of claim 1 having the formula

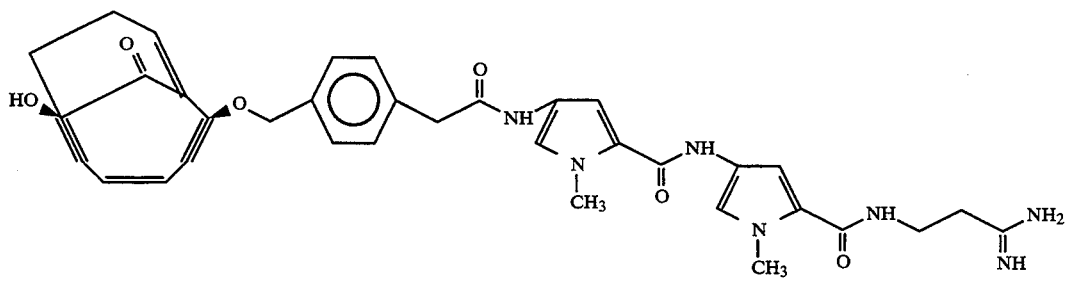

or a pharmaceutically acceptable salt thereof.

8. A compound of claim 1 having the formula

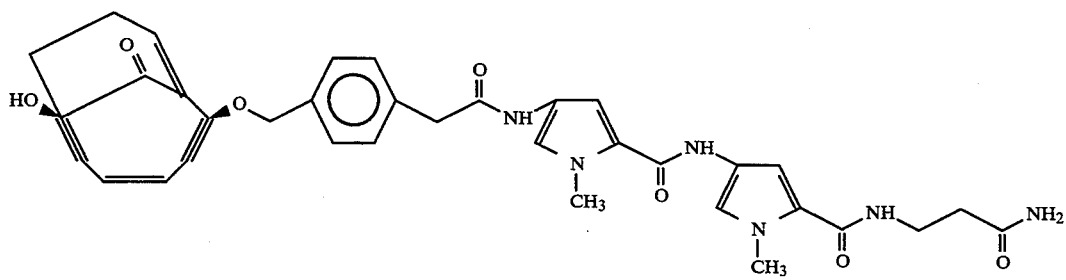

9. A compound of claim 1 having the formula or a pharmaceutically acceptable salt thereof.

10. A compound of claim 1 having the formula

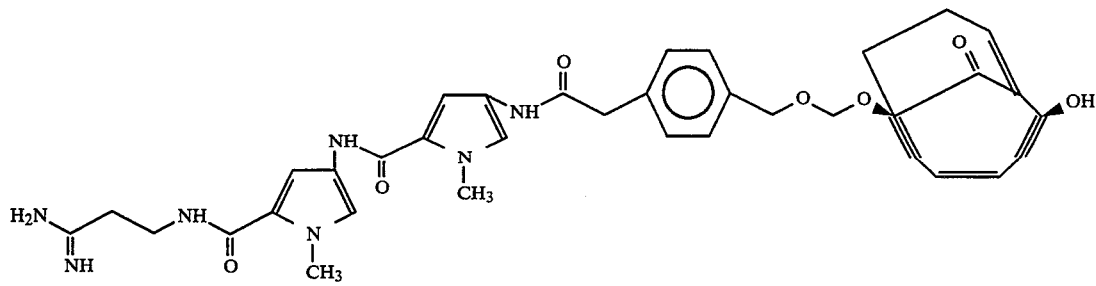

or a pharmaceutically acceptable salt thereof.

11. compound of claim 1 having the formula

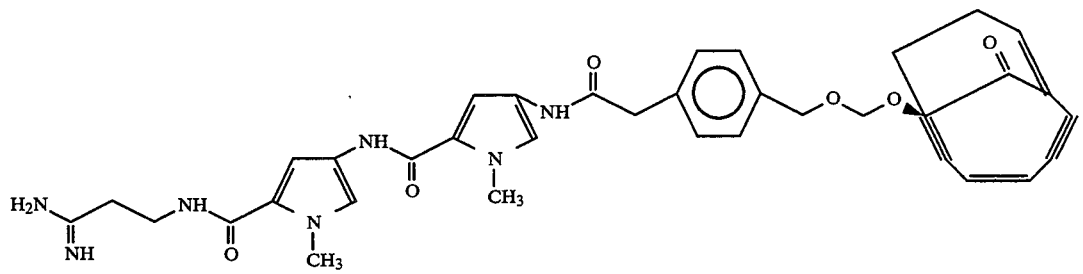

12. A pharmaceutical composition which comprises an antitumor effective amount of a compound of claim 1 and a pharmaceutically acceptable carrier.

13. A method for inhibiting leukemia or human colon carcinoma in a mammalian host which comprises administering to said host an effective leukemia or human colon carcinoma inhibiting amount of a compound of claim 1.

* * * * *